United States Patent [19]

Buter et al.

[11] Patent Number: 5,580,966
[45] Date of Patent: Dec. 3, 1996

[54] PROCESS FOR THE SYNTHESIS OF POLYOL FATTY ACID POLYESTERS

[75] Inventors: Markus G. Buter, Vlaardingen; Bart Barmentlo, Delft; Ulrich Eicken, The Hague, all of Netherlands

[73] Assignee: Unilever Patent Holdings B.V., Vlaardingen, Netherlands

[21] Appl. No.: 244,538

[22] PCT Filed: Nov. 26, 1992

[86] PCT No.: PCT/EP92/02743

§ 371 Date: Sep. 6, 1994

§ 102(e) Date: Sep. 6, 1994

[87] PCT Pub. No.: WO93/11141

PCT Pub. Date: Jun. 10, 1994

[30] Foreign Application Priority Data

Nov. 29, 1991 [EP] European Pat. Off. .............. 91203139

[51] Int. Cl.$^6$ .............................. C07H 1/00; C07H 13/04
[52] U.S. Cl. ........................................... 536/18.6; 536/112
[58] Field of Search ..................... 536/18.6, 119

[56] References Cited

U.S. PATENT DOCUMENTS

| | | | |
|---|---|---|---|
| 3,963,699 | 6/1976 | Rizzi et al. | 260/234 R |
| 4,517,360 | 5/1985 | Volpenhein | 536/119 |
| 4,973,682 | 11/1990 | Willemse | 536/119 |
| 5,043,438 | 8/1991 | Buter | 536/119 |

FOREIGN PATENT DOCUMENTS

| | | |
|---|---|---|
| 323670 | 7/1989 | European Pat. Off. . |
| 383404 | 8/1990 | European Pat. Off. . |

OTHER PUBLICATIONS

WO,A,9 204 360—Mar. 19, 1992—see p. 15, line 3—p. 16, line 10.

*Primary Examiner*—Gary L. Kunz
*Attorney, Agent, or Firm*—Cushman Darby & Cushman, L.L.P.

[57] ABSTRACT

The present invention pertains to a process for the production of polyol fatty acid polyesters by reacting a reactant mixture of polyol, a fatty acid lower alkyl ester, a transesterification catalyst and an alkali metal soap emulsifier. The process comprises removing non-dissolved alkali metal soap from the reaction mixture at a degree of transesterification of more than 60%, preferably 65–90%, and recycling the alkali metal soap that is removed during the transesterification to the starting reactant mixture. The invention is applicable both to a batch-wise polyol polyester synthesis and to a continuous synthesis.

11 Claims, No Drawings

PROCESS FOR THE SYNTHESIS OF POLYOL FATTY ACID POLYESTERS

The present invention relates to a process for the production of polyol fatty acid polyesters wherein a reaction mixture of a polyol and/or fatty acid oligoesters thereof, a fatty acid lower alkyl ester, a transesterification catalyst and an alkali metal soap emulsifier is caused to react under transesterification conditions and the alkali metal soap level is reduced during the transesterification reaction.

By "polyol" is meant any aliphatic or aromatic compound which comprises at least four free hydroxyl groups. In particular such polyols include the group of sugar polyols, which comprise the sugars, i.e. the mono-, di- and polysaccharides, the corresponding sugar alcohols and the derivatives thereof having at least four free hydroxyl groups. Examples of sugar polyols include glucose, mannose, galactose, xylose, fructose, sorbose, tagatose, ribulose, xylulose, lactose, maltose, raffinose, cellobiose, sucrose, erythritol, mannitol, lactitol, sorbitol, xylitol and α-methylglucoside. A preferred sugar polyol is sucrose.

In this specification by "polyol fatty acid polyester" is meant any such polyesters or mixtures thereof having a degree of conversion of at least 80%, in particular at least 90%. The degree of conversion is defined as the percentage of polyol hydroxyl groups of the polyol fatty acid polyester that on an average have been esterified with fatty acids. Thus a degree of conversion of 100 % corresponds to the fully esterified polyol.

In this specification by "fatty acid" are meant $C_8$–$C_{24}$ fatty acids which may be saturated or unsaturated, and may have straight or branched alkyl chains.

The polyol fatty acid polyesters are known to be suitable low-calorie fat-replacers in edible products. They are substantially indigestible for human beings while they have physical and organoleptic properties very similar to triglyceride oils and fats conventionally used in edible products. Polyol fatty acid polyesters are further reported to have use as pharmaceutical agents in view of their ability to absorb fat-soluble substances, such as in particular cholesterol, in the gastrointestinal tract, and remove these substances from the human body.

In general polyol fatty acid polyesters are synthesized by a process in which a polyol, such as a mono- or disaccharide, is reacted with a fatty acid lower alkyl ester, often the fatty acid methyl ester, in the presence of a transesterification catalyst, such as e.g. an alkali metal hydroxide or carbonate. In a first stage a polyol fatty acid mono- or oligoester is formed, which in a second stage or further stages is reacted to form polyesters of the desired degree of conversion. Under certain conditions the two stages of the reaction can be combined into a single reaction.

Processes of this type are described e.g. in U.S. Pat. No. 3,963,699, U.S. Pat. No. 4,517,360, U.S. Pat. No. 4,518,772, EP-A-254376, EP-A-256585 and EP-A-301634.

An often necessary component in the initially heterogeneous reaction mixture, also referred to as "premix", is an emulsifying or dispersing agent, such as in particular an alkali metal soap. Although it is essential in the initial phase of the transesterification reaction, soap causes a number of problems towards the end of the reaction, in particular when the reaction is carried out on a technical scale. A major problem is that with increasing degrees of conversion to polyester, soap tends to separate out resulting in a high viscosity of the reaction mixture and consequently poor mixing, slow release of the lower alkyl alcohol and therefore prolonged reaction times. A further problem connected to the separating out of the soap emulsifier is that of soap deposition on equipment parts, such as the reaction vessel.

Removal of the soap emulsifier from the crude fully converted (≧90%) reaction mixture is a laborious and costly step because of the large amounts of expensive chemicals used, such as phosphoric acid or citric acid. Moreover, the soap removal is largely responsible for the effluent produced during the refining of the polyol polyester produced.

European Patent Application 323670 describes a process for the production of polyol fatty acid polyesters wherein a reduction of the alkali metal soap level during the transesterification reaction is carried out at a degree of conversion of from 15 to 60%.

An effective reduction of the alkali metal soap level at that stage of the transesterification reaction, however, requires the use of an extractant in which the alkali metal soap dissolves, in particular aqueous solutions ($H_2O$, $H_2O$/NaOH, etc), with the concomitant need to lower the temperature of the reaction mixture, to dry the extracted reaction mixture, because water is a catalyst poison at elevated temperatures and causes saponification, and to add fresh transesterification catalyst after the soap extraction, since catalyst is largely extracted together with the soap.

It was found that the problems related to the presence of high soap levels in the reaction product can be overcome and important savings in raw material and reduction of process costs can simultaneously be achieved by recycling the soap removed at an advanced stage of the transesterification reaction. An advanced stage of the reaction is to be understood as corresponding to a degree of conversion of more than 50%, in particular more than 60%.

Accordingly, the present invention in its main aspect provides a process for the production of polyol fatty acid polyesters by reacting a mixture of a polyol and/or fatty acid oligoesters thereof, a fatty acid lower alkyl ester, a transesterification catalyst and an alkali metal soap emulsifier under transesterification conditions and reducing the alkali metal soap level during the transesterification reaction, wherein the alkali metal soap that is removed is recycled to said mixture of polyol and/or fatty acid oligoesters thereof, fatty acid lower alkyl ester, transesterification catalyst and alkali metal soap emulsifier.

It was found that a substantial part of the alkali metal soap is not dissolved in the reaction mixture when the degree of conversion is high, especially above 60%, whereas at lower degrees of conversion, e.g. below 50%, the alkali metal soap is still largely or completely dissolved.

Accordingly, the present invention also provides a process for the production of polyol fatty acid polyesters by reacting a mixture of a polyol and/or fatty acid oligoesters thereof, a fatty acid lower alkyl ester, a transesterification catalyst and an alkali metal soap emulsifier under transesterification conditions and reducing the alkali metal soap level during the transesterification reaction, wherein nondissolved alkali metal soap is removed at a degree of transesterification of more than 60%.

In general, the step of reducing the alkali metal soap level of the transesterification mixture is carried out at a degree of conversion of 60–100%, preferably 65–99%, more preferably 65–90% and most preferably at a degree of conversion of 70–85%.

The main aspect of the invention allows the use of low ratios of alkali metal soap to polyol in the starting transesterification mixture, i.e. it allows a smaller amount of fresh. i.e. non-recycled soap to be added in the starting reaction mixture. Thus, the non-recycled alkali metal soap and the polyol and/or fatty acid oligoesters thereof are preferably added in a molar ratio of from about 0.01 to less than 0.5. In particular, a process is provided wherein the alkali metal soap and the polyol and/or fatty acid oligoesters thereof are added to the starting mixture in a molar ratio of about 0.02 to less than 0.35, most preferably in a molar ratio of about 0.05 to 0.2. The molar ratio of total alkali metal soap to polyol and/or fatty acid oligoesters added to the starting mixture is advantageously between 0.1 and 0.8, preferably between 0.2 and 0.7 and especially between 0.3 and 0.6. The molar ratio of non-recycled to recycled soap is preferably below 1.5, more preferably between 0.1 and 1, most preferably between 0.2 and 0.8.

An important advantage of this embodiment of the invention is that recycling of the alkali metal soap to the initial mixture of polyol and/or fatty acid oligoesters thereof, fatty acid lower alkyl ester, transesterification catalyst and alkali metal soap emulsifier, results in considerable savings in soap feed. At the same time, undissolved polyol is returned to the initial stage, thus leading to savings in polyol starting material as well. As a further advantage, some partially esterified polyol will be recycled together with the soap, resulting in an improved emulsifying power of the recycled material and thus in a further reduction of required soap feed.

The alkali metal soap that is removed during the transesterification reaction may contain amounts of other reaction components, such as partly or wholly esterified polyol, transesterification catalyst and fatty acid lower alkyl ester, which could result in product loss or would require additional separation steps. When the non-dissolved soap fraction removed is recycled to the starting mixture, there is no need to separate these other components, which further contributes to an efficient use of starting materials.

The amount of non-dissolved alkali metal soap that is removed during the reaction corresponds to at least 25% by weight of the total amount of soap present in the reaction mixture. Preferably, the amount is at least 50% of the total amount of soap.

The alkali metal soap may be removed at temperatures which are about equal to the transesterification temperatures. Lower temperatures are also possible, but they are not preferred because of energy losses. Temperatures within the range of 60° and 135° C., especially within the range of from 100° to 130° C., were found to be suitable to maximize the relative amount of non-dissolved soap and to minimize problems of sludging in the separating equipment. Most preferred temperatures for soap removal are from 110°–115° C.

The reduction of the soap level in the reaction mixture may be carried out by any suitable refining method which avoids the use of aqueous solutions. Such methods include in particular mechanical means, such as separation by centrifuge, hydrocyclon or filter, of that part of the soap already separated out. The use of a centrifuge or a decanter was found to be advantageous, since possible losses of solid material can be minimized. The separation apparatus used for removing alkali metal soap can be of a batch type or of a continuously operating type.

The transesterification reaction is suitably carried out at a temperature within the range of from 100° to 180° C. Preferred temperatures are within the range of from 110° to 160° C., the range of from 120° to 150° C., in particular 130° to 140° C., being preferred most.

The transesterification reaction may be carried out using a two-step transesterification, such as described in EP-A-290966 (U.S. Pat. No. 4,973,682) and EP-A-383404 (U.S. Pat. No. 5,043,438). The transesterification reaction may be carried out in a batch process or in a continuous process as described in EP-A-383404.

In general the transesterification reaction is carried out under conditions of reduced pressure so as to remove the lower alkyl alcohol formed from the fatty acid lower alkyl ester during the transesterification. Particular pressure conditions are a resultant of both process engineering and economic considerations. The reaction is advantageously carried out at reduced pressures in terms of the partial vapour pressure of the lower alkyl alcohol. Suitably such partial vapour pressures in a first reaction zone are reduced to levels within the range of from 20 to 200 mbar, pressures of from 35 to 150 mbar and especially 40 to 120 mbar being preferred.

During the subsequent stages of the reaction it is preferred to apply pressures as low as possible within the constraints of economic processing in order to drive the transesterification to high degrees of conversion. Preferred partial lower alkyl alcohol pressures during the final stages are below 50 or 25 mbar or even below 10 or 5 mbar. These pressures may be achieved by gradual pressure reduction over time in a batch-wise process, but also by a step-wise pressure reduction over two or more reaction zones in a continuous process.

Particularly during the final stage of the transesterification reaction, a preferred method for reducing the partial vapour pressure of the lower alkyl alcohol is to use a stripping agent to ensure adequate removal of the lower alkyl alcohol formed during the transesterification. Suitable stripping agents comprise inert gases such as nitrogen and food-grade hydrocarbons, in particular hexane. The use of a stripping agent is described in EP-A-349059.

It is preferred to apply agitation to the reaction mixture, in particular throughout the initial stage of the reaction e.g. by way of stirring means in the reaction vessel.

Suitably, the lower alkyl alcohol formed during the transesterification reaction from the lower alkyl ester is condensed in suitable condenser means after the removal thereof from the reaction mixture, and collected for subsequent use or re-use.

In general the reactants used in the transesterification reaction in accordance with the process of the present invention comprise a polyol and/or fatty acid oligoester thereof, a fatty acid lower alkyl ester, a transesterification catalyst, and an emulsifier. Preferred emulsifiers are alkali metal soaps. Other alkali-resistant emulsifiers can also be used, such as edible emulsifiers including phosphatides, such as lecithin, mono- and di-glycerides and sugar oligoesters of fatty acids, in particular mono- and di-esters, and detergents, such as alkali metal alkyl sulphates.

In the preparation of the mixture of reactants also solvents, such as water and/or lower alkyl alcohols, may optionally be introduced separate from or together with one or more of these reactants.

The polyol can be any of those as defined hereinbefore, or a mixture thereof. Preferred polyol starting materials are the sugar polyols, and in particular sucrose. The polyol starting material does not necessarily consist solely of non-esterified polyols. It may in addition or instead comprise polyol oligoesters of fatty acids, such as mono-, di- and/or triesters, which are intermediates in the conversion of polyols to the polyol fatty acid polyesters. In case of soap recycling, even higher polyol esters (up to fully esterified polyols) may be present in the starting mixture.

Suitable fatty acid lower alkyl esters are fatty acid esters of the group of lower alcohols including mono-, di- and triols and ether-alcohols. In particular, the ester is derived from the $C_1$–$C_5$ mono-alcohols or methoxymethanol, preferably methanol. The fatty acid residues can be any of those as defined hereinbefore, the selection of which is dependent of the specific polyol fatty acid esters desired.

The amount of fatty acid lower alkyl ester is dependent on the desired degree of conversion. In the synthesis of polyol polyesters having high degrees of conversion in general excess amounts of fatty acid lower alkyl ester are used. When fully converted sucrose polyesters are aimed at, good results are obtained when a molar ratio of fatty acid lower alkyl ester to sucrose is used within the usual range of from 10:1 to 20:1.

However, the present process allows the use of lower amounts of fatty acid lower alkyl ester, even in the final stage of the reaction, because of the reduced viscosity resulting from the soap removal and because of the corresponding enhanced reaction rates. Thus amounts between the stoichiometrical amount with respect to the polyol or oligoester thereof and an excess of about 60% of that amount, i.e. in a molar ratio of acyl groups of the fatty acid lower alkyl ester to free hydroxy groups of the polyol or oligoester thereof of between 1 and 1.6 can be used. In particular, a molar ratio corresponding to a molar ratio of acyl groups to free hydroxy groups of between 1.1 and 1.5 may be used. When sucrose is used as the starting polyol, this means a molar ratio of fatty acid lower alkyl ester to sucrose within the range of from 8:1 to 13:1, preferably about 9:1 to 12.5:1, most preferably about 10:1 to 12:1.

Suitable transesterification catalysts include the group consisting of alkali metals, alkaline earth metals, and alloys thereof, as well as the alkoxides, bicarbonates, carbonates, hydrides, and hydroxides of such metals. KOH has been found to be particularly suitable, but also NaOH and the corresponding carbonates, and bicarbonates of potassium or sodium can be advantageously used. Although one might argue that the above reagents are not the catalysts themselves, but are reagents forming the catalyst, in this specification, as is done in the literature relating to similar processes, this group will be referred to as catalysts.

The catalyst is used in an amount corresponding to a molar ratio of catalyst: polyol of at least 0.01:1, and preferably in the range of 0.05:1 to 1:1. Particularly efficient catalyst to polyol ratios lie within the range of 0.1 to 0.3, best results having been found with ratios within the range of 0.2 to 0.3.

In order to ensure contact between the various reactants, particularly in the early stages of the reaction, the reaction mixture further comprises an emulsifier, preferably an alkali metal soap derived from any of the fatty acids, or another emulsifier as defined hereinbefore. A part of the fatty acid soap emulsifiers may be derived from short chain fatty acid soap having a fatty acid chain length of less than 15 carbon atoms, such as coconut soap, to reduce viscosity at the final stage of the transesterification reaction which is known to occur in prior art batch processes.

In the present process, however, the use of such short chain fatty acid soaps is not necessary; the removal of a substantial part of the soap at high conversion rates sufficiently lowers the viscosity to obviate the presence of low viscosity, i.e. short chain, soap emulsifiers. Thus the alkali metal soap emulsifier to be used according to the invention may be derived from substantially the same fatty acid(s) as the fatty acid lower alkyl ester. This conveniently avoids the need to separate the short chain fatty acid residues from the excess fatty acid lower alkyl ester recovered from the final reaction mixture.

The alkali metal soap emulsifier may also be introduced into the reaction mixture in the form of a precursor thereof, such as the corresponding free fatty acids. In such a case the composition of the reactant mixture should be such that the precursor is converted into the corresponding alkali metal soap after addition to and mixing with the reactant mixture.

When free fatty acids are used as emulsifier precursors, an alkaline material should be present in the reaction mixture suitable to convert the fatty acid precursor into the corresponding soap emulsifier. Suitably, the transesterification catalyst can be used to effect such a conversion. Accordingly, the amount of catalyst should be sufficient to ensure both proper catalytic action during the esterification, as discussed hereinbefore, and full neutralization of such a soap precursor to the corresponding soap.

Suitable amounts of emulsifier lie within the range of from 0.1 to 15% by weight, preferably of from 0.1 to 10%, and most preferably of from 0.2 to 4% by weight of the total reactant mixture, depending on the ratio of fatty acid lower alkyl ester to polyol. The amount of emulsifier can also conveniently be related to the amount of polyol introduced into the reactant mixture. A soap/polyol molar ratio of about 0.4 to 0.7 in the reactant mixture and in the reaction zones can suitably be used in the present process. Preferably, a part of the soap is derived from recycling so that the ratio of freshly added soap to polyol will be less than 0.4. In a particular embodiment of the invention an added soap/polyol molar ratio of less than 0.35, in particular about 0.2 or less is used.

Optionally, one or more solvents may be introduced separate from or together with the various reactants to improve addition and mixing thereof. Suitable solvents include water and/or lower alcohols, such as $C_1$–$C_5$ alcohols, in particular methanol. The solvent is subsequently removed before or at the start of the transesterification reaction.

Advantageously, the reaction mixture is spray-dried before starting the esterification reaction to achieve a homogenized and substantially solvent-free reaction mixture which is particularly suitable as starting mixture for the subsequent esterification in accordance with the present invention.

In this specification the term "homogenized" means intimately mixed and is not restricted to homogenized in a narrow microscopic sense.

By "substantially solvent-free" is meant comprising less than 0.5% of solvent. Solvent levels at the start of the esterification reaction of less than 0.1, or even 0.05% are preferred.

Spray-drying is suitably effected by passing the initial mixture of reactants through a spraying nozzle into a drying chamber. Intimate mixing occurs due to the dissipation of energy on passing through the spraying nozzle. Evaporation of the solvent occurs in the drying chamber, the resulting vapour continuously being removed from the drying chamber by suitable reduced pressure or gas flow conditions. Adequate solvent evaporation may be established by a variety of per se conventional techniques, including the application of reduced pressure and/or elevated temperature conditions, or the use of, optionally heated, co-current, counter-current or mixed-current inert gas flows.

In a batch-wise operation the drying chamber is also suitably used as reaction vessel for the transesterification reaction. In a continuous or semi-continuous operation the drying chamber and reaction vessel preferably are separate.

It may be of further advantage to pre-mix the reactants before passing through the spraying nozzle by an alternative agitation step for example employing a dynamic or static mixer, or flow restriction in the feed line to the spraying nozzle.

It is preferred to prepare the reactant mixture by way of the following process. In an initial step the polyol or the fatty acid oligoester thereof is mixed with the catalyst in a liquid system so as to form the corresponding polyol anion. The formation of the actual polyol anion may be immediate or only be realized under substantially solvent-free conditions.

Preferably, the contact between the polyol or the oligoester thereof and the catalyst are mixed in the presence of a solvent, which is subsequently removed in the spray-drying step in accordance with the present invention. Most preferably, the polyol or the oligoester thereof and the catalyst are first partially or fully dissolved in a solvent and subsequently mixed. Suitable such solvents include water, lower alcohols and mixtures thereof. In particular water is a suitable solvent if potassium or sodium hydroxide is used as the transesterification catalyst.

In a subsequent step this liquid system is added to the fatty acid lower alkyl ester, optionally in combination with the emulsifier. After addition to the fatty acid lower alkyl ester the resulting reaction mixture may be conveniently spray-dried.

Although alkali metal soaps or suitable precursors thereof are suitable emulsifiers in terms of the esterification reaction a drawback that may be attached to the use of soaps is the fact that the spray-drying thereof necessitates relatively frequent cleaning of the spray-drying equipment. In particular on a technical scale this is undesirable. Accordingly, it is preferred to add the soap emulsifiers or precursors thereof, to the reaction mixture only after the spray-drying step. Using this route the relatively frequent cleaning of the spray-drying equipment can be avoided.

The degree to which desolvatization is achieved in the spray-drying step is the resultant of economic and engineering factors, such as in particular the amount of solvent to be removed and the corresponding energy input or temperature required in the drying chamber. Accordingly, instead of using spray-drying conditions resulting in full removal of solvent, it may be of advantage to have the spray-drying step followed by a further 'post-drying' treatment which drives the removal of residual solvent to substantial completion. Any such conditions resulting in evaporation of any residual solvent still present after spray-drying or introduced in the post spray-drying addition of the emulsifier component, may be suitable and include temperature and reduced pressure conditions, stripping with suitable stripping agents, such as preferably methanol, or inert gases, such as nitrogen, or submitting the reaction mixture to a further spray-drying step.

Suitably the solvent level of the reaction mixture is reduced to below 0.5% in the spray-drying step and further reduced to below 0.1% in the subsequent post-drying step. Preferably, the solvent level is reduced to below 0.1% in the spray-drying step and to below 0.05% in the post-drying step. If so desired a supplementary amount of polyol may be introduced into the starting mixture of reactants before starting the transesterification reaction.

Although the process of the present invention is suitable for the synthesis of polyol fatty acid esters of the general group as defined hereinbefore, it is particularly suitable for the synthesis of polyol fatty acid polyesters esterified to at least 95% degree of conversion, preferably derived from the sugar polyols selected from the group of disaccharides or the alcohol derivatives thereof, such as sucrose.

Preferred embodiments of the invention will now be illustrated with reference to the following examples, all percentages being by weight unless indicated otherwise.

EXAMPLE 1 a. Hermetic pilot centrifuge.

Type of centrifuge: hermetic pilot centrifuge (Westfalia TA1-48-525)

Feed-stock: crude sucrose polyester of partially hardened soybean oil (moB028) (transesterification conditions: fatty acid methyl ester: sucrose≈14; soap: sucrose≈0.5; catalyst: sucrose 0.2–0.25) with 4.6% of soap and conversion levels ranging from about 50% to 80%.

Centrifuge temperature: approximately 120° C.

Throughput: approximately 30 kg/h.

At an OH-value of 48 (≈50% conversion) no soap could be separated from the feed-stock by centrifugation in a batch laboratory centrifuge: all soap (4.6%) was dissolved. At lower OH-values of 19–22, corresponding to conversion levels of 77–80%, only some 2.2% of soap remained dissolved after centrifugation in the hermetic pilot centrifuge, coinciding very well with the equilibrium solubilities found in the batch laboratory centrifuge (≈2.1%).

b. Further reaction.

The material obtained from the hermetic pilot centrifuge (see a.) was further reacted under full vacuum. Both materials (ex moB028) had an initial OH-value of 18, corresponding to a conversion level of 81%. After 5 h the conversion of the centrifuged material had increased to 90%.

EXAMPLE 2 a. Self-desludging centrifuge (manual total desludging).

Type of centrifuge: continuous self-desludging disk-stack centrifuge (Westfalia SA-1-02-575).

Feed-stock: crude sucrose polyester of hardened palm oil (weakening point 58° C.) and palm kernel oil (weakening point 39° C.) (=P058/PK39) (esterification conditions: as in example 1) with 4.2% of soap and a conversion level of 80%.

Centrifuge temperature: approximately 77° C.

Throughput: varying from 60 to 190 kg/h.

In the self-desludging centrifuge operated with manual total desludging the amount of soap could be decreased from 4.2% in the feed-stock (OH-value=19, corresponding to 80% conversion) to 1.2% on an average in the out-going oil phase, resulting in a soap stock containing approximately 22% of soap. The separation was independent of the throughput at throughputs up to 140 kg/h. At higher throughputs the separation was negatively influenced.

b. Self-desludging centrifuge (automated partial desludging).

Type of centrifuge: continuous self-desludging disk-stack centrifuge (Westfalia SA-1-02-575).

Feed-stock: crude sucrose polyester from P058/PK39 (esterification conditions as in example 1) with 5.3% of soap and a conversion level of >96%.

Centrifuge temperature: approximately 70° C.

Throughput: varying from 95 to 270 kg/h.

In the self-desludging centrifuge operated with automated partial desludging the amount of soap could be decreased from 5.3% in the feed-stock (>96% conversion) to 0.2% in the out-going oil phase, resulting in a soap stock containing approximately 21% of soap. The separation was independent of the throughput at throughputs of 180 kg/h and lower. At higher throughputs the separation was negatively influenced.

EXAMPLE 3

Decanter.

Type of centrifuge: continuous decanter (Westfalia CA-220-00-00)

Feed-stock: crude sucrose polyester from PO58/PK39 (esterification conditions as in example 1) with 4.2% of soap and a conversion level of 80%.

Centrifuge temperature: either 75° or 98° C.

Throughput: varying from 270 to 1450 kg/h.

In the decanter operated at 75° C. it was possible to decrease the amount of soap from 4.2% in the feed-stock (OH-value=20, corresponding to 80% conversion) to about 1.05% in the out-going oil phase, resulting in a soap stock containing approximately 46% of soap. The separation was independent of the throughput at throughputs up to 600 kg/h. At higher throughputs the separation was slightly negatively influenced.

In the decanter operated at 98° C. it proved to be possible to decrease the amount of soap from 4.2% in the feed-stock (OH-value=20, corresponding to 80% conversion) to about 1.0% in the out-going oil phase, resulting in a soap stock containing approximately 47% of soap. The separation was independent of the throughput at throughputs up to 1300 kg/h. At higher throughputs the separation was less efficient.

EXAMPLE 4

Materials:

The following raw materials were mixed to form a premix:

sucrose/potassium sucrate slurry, consisting of 94.60% fatty acid methyl ester (FAME), 3.96% potassium sucrate and 1.43% sucrose;

soap slurry (same batch code), consisting of 91.0 % FAME and 9.0% coconut soap;

pure sucrose;

FAME (All FAME was made from moB028 (see example 1) and distilled).

The concentrations of the various ingredients were determined by common analyses (OH number, titration of strong base & soap content).

Equipment:

The raw materials were reacted in a continuous line comprising the following items:

feed storage tank, stirred, blanketed with nitrogen;

dosing pump determining the mass flow of reaction mixture through the line;

two continuous stirred tank reactors (CSTR) in line, each equipped with a stirrer, a nitrogen sparger ring, and a discharge pump maintaining a constant level in the reactor;

(batch) lab centrifuge type Sorvall SS-4 (max. 13,000 rpm).

TABLE 1

| | experiment | | | | | |
|---|---|---|---|---|---|---|
| | #1 | | #2 | | #3 | |
| | P | M | P | M | P | M |
| exp. period[1] | 33 h | | 11 h | | 36 h | |
| $N_{OH}$ in premix | 103 ± 9 | | 126 ± 6 | | 113 ± 4 | |
| $\Phi_L$ [L/h] | 0.71 | | 0.56 | | 0.53 | |
| V [L] | 1.8 | 0.9 | 1.7 | 1.0 | 1.8 | 1.05 |
| τ [h] | 2.5 | 1.3 | 3.0 | 1.8 | 3.4 | 2.00 |
| $\Phi_G$ [L/h] | 100 | 1400 | 185 | 1330 | 195 | 1380 |
| F | 130 | 1970 | 329 | 2362 | 371 | 2624 |
| $F/N_{OH}$ | 1.3 | 19.1 | 2.6 | 18.7 | 3.3 | 23.2 |
| $\tau_{total}$ [h] | 3.8 | | 4.9 | | 5.4 | |
| $t_{cycle}$ [h][2] | 7.8 | | 8.9 | | 9.4 | |

TABLE 1-continued

| | experiment | | | | | |
|---|---|---|---|---|---|---|
| | #1 | | #2 | | #3 | |
| | P | M | P | M | P | M |

P = prereactor; M = main reactor
$\Phi_L$ = liquid volume flow
$\Phi_G$ = gas volume flow
τ = mean residence time
F = strip factor = $\Phi_G/\Phi_L$
$N_{OH}$ = OH number
V = volume
[1] after steady state was reached.
[2] total mean residence time plus mean soap recycling time, i.e. 0.5 h standing, 2 h centrifugation and standing, and 1.5 h in the feed tank as part of the premix.

Procedure:

Two runs were made in a continuous synthesis mode combined with batch-wise centrifugation and batch-wise premix preparation. Each run was started with a premix containing only original soap. Every hour the product was centrifuged, and every three hours a new premix was mixed from the components. The mixing ratios of the components were calculated after measuring the soap and strong base content of the recycling soap slurry to be used. The two reactors were operated at 135° C. and atmospheric pressure and stripped with nitrogen. The main reactor product was centrifuged at approximately room temperature and without any inert gas blanketing. The reaction conditions for the three experiments are summarized in table 1.

Three experiments were carried out during these two runs, using the following premixes:

| | experiment | | |
|---|---|---|---|
| | #1 | #2 | #3 |
| molar FAME/sucrose ratio | 13.1 | 10.4 | 11.7 |
| original soap/recycled soap ratio | 0.67 | 0.67 | 1.5 |
| molar soap/sucrose ratio | 0.58 | 0.51 | 0.55 |
| molar KOH/sucrose ratio | 0.28 | 0.27 | 0.27 |

At the start of each run, i.e. while the feed was normal premix, and at the end of every experiment, centrifuged (or in some cases uncentrifuged) product was collected (≈1 kg each) and further reacted batchwise in order to obtain a fully converted SPE for comparison of the different products on reactivity in the last step, by-product content, and refining properties.

The dissolved content of the main reactor was proportional to the OH number, roughly according to the equation: [soap, wt.-%]=0.08 $N_{OH}$. The average OH numbers and catalyst and soap contents of the prereactor and main reactor products and the soap slurry and the share of main reactor product obtained as soap slurry are summarized in table 2.

The following products were collected from the main reactor and further reacted batch-wise to OH-numbers ≦5.0:

1. after 5–7 h of first run, from normal premix, centrifuged;

2. after 19–22 h of first run, after 8–11 h of exp. #1, centrifuged;

3. after 38–42 h of first run, after 27–31 h of exp. #1, centrifuged;

4. after 0–2 h of second run, from normal premix, not centrifuged;

5. after 2–5 h of second run, from normal premix, centrifuged;

6. after 34–45 h of second run, after 0–11 h of exp. #2, centrifuged;
7. after 91–94 h of second run, after 31–34 h of exp. #3, centrifuged;
8. after 94–96 h of 2nd run, after 34–36 h of exp. #3, not centrifuged.

Products 1, 4 and 5 are thus reference products without soap recycling.

When the soap removal and the last stage of the reaction were carried out batch-wise (as on laboratory scale) the quality of the final product was different from one batch to another; in a continuous mode no such differences occur.

TABLE 2

Results of the three internal soap recycling experiments
(mean values, calculated over the whole experimental period)

| | experiment | | | | | |
|---|---|---|---|---|---|---|
| | #1 | | #2 | | #3 | |
| | n.c.[1] | c.[1] | n.c. | c. | n.c. | c. |
| prereactor | | | | | | |
| 2OH number[2] | 61 | 48 | 72 | 73 | 65 | 64 |
| conversion degree[3] [%] | 47 | | 42 | | 44 | |
| main reactor | | | | | | |
| OH number[2] | 36 | 13 | 38 | 39 | 31 | 31 |
| conversion degree[3] [%] | 84 | | 69 | | 73 | |
| catalyst content [wt-% KOH] ± 30% | 0.18 | 0.03 | 0.15 | 0.07 | 0.11 | 0.07 |
| soap content [wt-%] ± 10% | 3.8 | 1.0 | 5.0 | 3.2 | 5.3 | 2.4 |
| soap slurry | | | | | | |
| soap content [wt-%] | 10.8 | | 12.3 | | 9.7 | |
| catalyst content [wt-% KOH] | 0.46 | | 0.30 | | 0.27 | |
| share of product [wt-%] | 32 | | 21 | | 40 | |

[1]c. = centrifuged; n.c = not centrifuged
[2]calculated without the amount of undissolved sucrose ($OH_{n.c.} - OH_c$.)

Refining

In order to study the effects of different internal soap recycling conditions, refining was carried out using a known procedure (see EP-A-435364) using silica and active carbon bleaching and deodorization.

Table 3 summarizes the analytical data of the crude and refined SPE. The soap content ranges from 0.5 to 6.17 wt %. Two batches with the lowest soap content (4 and 8) had the darkest colour. In general the crude SPE's with the lowest amount of soap give the best quality refined SPE. In contrast, batch no. 8 was difficult to refine with respect to soap removal. This was solved by including extra washing steps.

TABLE 3

Analytical data of crude SPE

| | Crude SPE | | | Refined SPE | | | |
|---|---|---|---|---|---|---|---|
| Batch no. | Soap [wt-%] | Poly-SPE [wt-%] | SPE [wt-%] | Poly-SPE [wt-%] | SPE [wt-%] | Yellow (2") | Red (2") |
| 1 | 0.9 | 0.5 | 52.6 | 1.0 | 96.6 | 5.8 | 1.2 |
| 2 | 1.1 | 0.8 | 51.4 | 1.6 | 95.6 | 15.5 | 2.4 |
| 3 | 0.5 | 0.3 | 43.8 | 0.7 | 96.3 | 6.0 | 1.2 |

TABLE 3-continued

Analytical data of crude SPE

| | Crude SPE | | | Refined SPE | | | |
|---|---|---|---|---|---|---|---|
| Batch no. | Soap [wt-%] | Poly-SPE [wt-%] | SPE [wt-%] | Poly-SPE [wt-%] | SPE [wt-%] | Yellow (2") | Red (2") |
| 4 | 5.9 | 1.5 | 66.3 | 2.1 | 95.5 | 32.0 | 4.9 |
| 5 | 4.4 | 0.8 | 50.9 | 0.4 | 96.3 | 19.0 | 2.8 |
| 6[1] | 3.9 | 1.3 | 73.4 | 2.2 | 94.3 | >40 | >9 |
| 7 | 2.4 | 1.1 | 75.4 | 1.6 | 96.3 | 12.0 | 2.1 |
| 8 | 6.2 | 0.2 | 71.9 | 0.8 | 95.5 | 39.0 | 5.7 |

[1]Reaction conditions of this batch were not optimal

These experiments show that a continuous SPE synthesis with soap recycling can be run under stable conditions for a long time. The soap content in the main reactor product can be reduced considerably (e.g. from 5% to 1%), provided the conversion degree is high. A linear correlation between conversion degree and dissolved soap concentration has been found. Crude SPE with decreased soap content gives refined SPE of better quality, as shown by the colour. Furthermore, major savings of raw materials (soap in starting mixture preparation, acid in refining) and refining effluent are obtained.

In summary, the process of the invention provides unexpected advantages including a simplified and therefore more economic refining process requiring less reagents such as acid and bleaching agents; reduced flows of waste materials; an improved synthesis process as a result of the recycling of fatty ester lower alkyl ester and polyol oligoester (reduced loss and improved mixing); and better product performances such as improved colour and reduced free fatty acid content of the product and in general a more stable product quality, which is very important when the polyol polyesters produced are used in food products.

We claim:

1. Process for the production of polyol fatty acid polyesters by transesterification reaction comprising reacting a mixture of a polyol, a fatty acid lower alkyl ester, a transesterification catalyst and an alkali metal soap emulsifier under transesterification conditions, removing alkali metal soap emulsifier during the transesterification reaction when the degree of transesterification is between 65–99% and recycling the alkali metal soap that is removed to another mixture of polyol, fatty acid lower alkyl ester and transesterification catalyst for further transesterification reaction.

2. Process according to claim 1, wherein recycled alkali metal soap and non-recycled alkali metal soap are added to said mixture and the molar ratio between non-recycled alkali metal soap and polyol thereof added to said mixture is between 0.02 and 0.35.

3. Process according to claim 2, wherein the molar ratio between non-recycled alkali metal soap and polyol added to said mixture is between 0.05 and 0.2.

4. Process according to claim 2, wherein the molar ratio between non-recycled alkali metal soap and recycled alkali metal soap added to said mixture is less than 1.5.

5. Process according to claim 2, wherein the molar ratio between non-recycled alkali metal soap and recycled alkali metal soap added to said mixture is less than 1.0.

6. Process according to claim 3, wherein the alkali metal soap is removed at a degree of transesterification of 70–85%.

7. Process according to claim 1, wherein at least 50% of the total amount of alkali metal soap present in the transesterification reaction is removed.

8. Process according to claim 1, wherein the alkali metal soap is removed by centrifuging and/or decanting.

9. Process according to claim 1, wherein the fatty acid lower alkyl ester and the polyol thereof are reacted in a molar ratio corresponding to a molar ratio of acyl groups of the fatty acid lower alkyl ester to free hydroxy groups of the polyol of between 1 and 1.6.

10. Process according to claim 1, wherein the alkali metal soap and the fatty acid lower alkyl ester are derived from substantially the same fatty acid(s).

11. Process according to claim 9, wherein the fatty acid lower alkyl ester and the polyol are reacted in a molar ratio corresponding to a molar ratio of acyl groups of the fatty acid lower alkyl ester to free hydroxy groups of the polyol of between 1.1 and 1.5.

* * * * *